(12) United States Patent
Ollerenshaw et al.

(10) Patent No.: US 11,471,677 B2
(45) Date of Patent: Oct. 18, 2022

(54) ARTICLE AND METHOD FOR TREATING DIABETIC PERIPHERAL NEUROPATHY

(71) Applicant: Avent, Inc., Alpharetta, GA (US)

(72) Inventors: Jeremy D. Ollerenshaw, Alpharetta, GA (US); Leah M. Roldan, Atlanta, GA (US); Elliot Blake Bourgeois, Huntsville, AL (US); Eric A. Schepis, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 16/469,182

(22) PCT Filed: Dec. 8, 2017

(86) PCT No.: PCT/US2017/065243
§ 371 (c)(1),
(2) Date: Jun. 13, 2019

(87) PCT Pub. No.: WO2018/125538
PCT Pub. Date: Jul. 5, 2018

(65) Prior Publication Data
US 2020/0023183 A1 Jan. 23, 2020

Related U.S. Application Data

(60) Provisional application No. 62/439,283, filed on Dec. 27, 2016.

(51) Int. Cl.
*A61N 1/36* (2006.01)
*A61N 1/04* (2006.01)

(52) U.S. Cl.
CPC ....... *A61N 1/36021* (2013.01); *A61N 1/0456* (2013.01); *A61N 1/0484* (2013.01);
(Continued)

(58) Field of Classification Search
CPC ................ A61N 1/0456; A61N 1/0484; A61N 1/36014; A61N 1/36017; A61N 1/36021;
(Continued)

(56) References Cited

U.S. PATENT DOCUMENTS 8,958,886 B2 2/2015 Schepis et al.
2004/0039417 A1 2/2004 Soykan et al.
(Continued)

FOREIGN PATENT DOCUMENTS

EP 2 517 755 A1 10/2012
JP 2005348859 A 12/2005
(Continued)

OTHER PUBLICATIONS

Tung, et al., "Analysis of electric field stimulation of single cardiac muscle cells", Biophysical Journal, vol. 63, dated Aug. 1992, 16 pages.
(Continued)

*Primary Examiner* — Carl H Layno
*Assistant Examiner* — Anh-Khoa N Dinh
(74) *Attorney, Agent, or Firm* — Meunier Carlin & Curfman LLC

(57) ABSTRACT

Articles and methods for non-invasively treating peripheral neuropathy via transcutaneous electrical stimulation of target nerve tissue are described. An exemplary article includes a support on which an electrode pair is positioned; a controller attached to the electrode pair via one or more leads; and a power supply connected to the controller. The article delivers electrical stimulation to the target nerve tissue via the electrode pair at a level sufficient to initiate vasodilation of vasculature within or adjacent the tissue. Meanwhile, the method includes positioning at least one electrode pair adjacent an area of skin overlying or in close proximity to the target nerve tissue and delivering electrical stimulation
(Continued)

to the tissue via the electrode pair. The electrical stimulation is delivered at a level sufficient to initiate vasodilation of vasculature within or adjacent the tissue. An implantable system and method for treating peripheral neuropathy via percutaneous electrical stimulation are also described.

28 Claims, 10 Drawing Sheets

(52) U.S. Cl.
CPC ..... *A61N 1/36017* (2013.01); *A61N 1/36034* (2017.08); *A61N 1/36153* (2013.01); *A61N 1/36157* (2013.01); *A61N 1/36171* (2013.01); *A61N 1/36175* (2013.01)

(58) Field of Classification Search
CPC ............ A61N 1/36034; A61N 1/36146; A61N 1/36153; A61N 1/36157; A61N 1/36171; A61N 1/36175; A61N 1/3787; A61N 1/36139
See application file for complete search history.

(56) References Cited

U.S. PATENT DOCUMENTS

| | | |
|---|---|---|
| 2005/0277997 A1 | 12/2005 | Ohta et al. |
| 2007/0255379 A1* | 11/2007 | Williams ................. A61N 1/05 607/120 |
| 2008/0195176 A1 | 8/2008 | Stefano et al. |
| 2009/0312676 A1* | 12/2009 | Rousso ..................... A61F 7/10 607/113 |
| 2013/0085420 A1* | 4/2013 | Feinstein ............. A61N 1/0468 601/5 |
| 2013/0317581 A1* | 11/2013 | Redington ......... A61N 1/36034 607/115 |
| 2014/0046423 A1* | 2/2014 | Rajguru .................. A61N 2/02 607/144 |
| 2014/0188194 A1* | 7/2014 | Schepis ................ A61N 1/0484 607/62 |
| 2016/0074668 A1* | 3/2016 | Nunez .................... A61N 5/025 607/101 |
| 2016/0121109 A1 | 5/2016 | Edgerton et al. |
| 2016/0184568 A1 | 6/2016 | Harris et al. |
| 2017/0173340 A1* | 6/2017 | Gupte ................. A61N 1/0558 |

FOREIGN PATENT DOCUMENTS

| | | |
|---|---|---|
| KR | 100994208 B1 | 11/2010 |
| WO | WO 2011/011748 A1 | 1/2013 |
| WO | WO 2014/151431 A2 | 9/2014 |
| WO | WO 2014/164438 A1 | 10/2014 |
| WO | 2016069687 A2 | 5/2016 |

OTHER PUBLICATIONS

Van Riper et al., "Electrical Field Stimulation-Medicated Relaxation of Rabbit Middle Cerebral Artery", American Heart Association Journals, dated Jan. 29, 1992, 10 pages.

International Search Report and Written Opinion for PCT/US2017/065243, dated Mar. 1, 2018, 15 pages.

Office Action, dated Jul. 26, 2022, received in connection with corresponding JP Patent Application No. 2019-534277 (English translation).

* cited by examiner

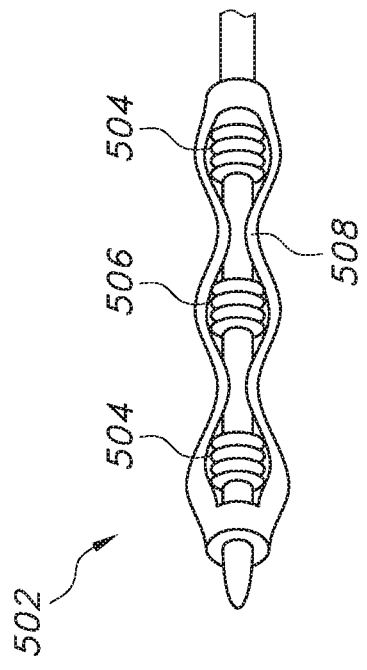
FIG. 11
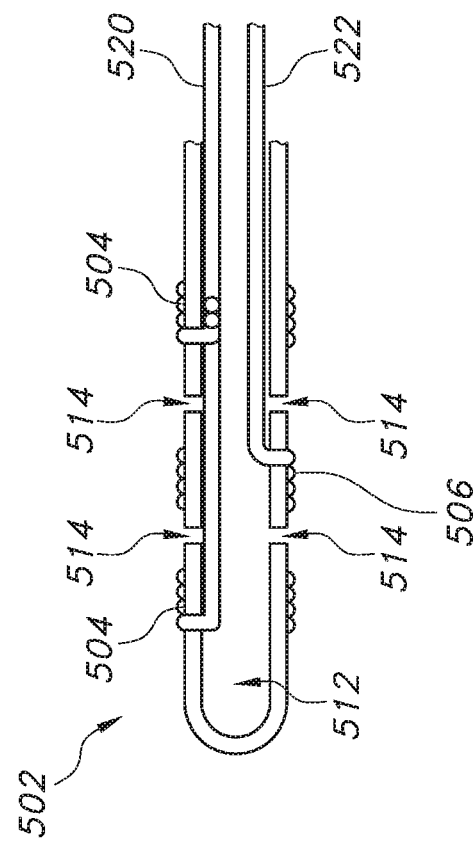
FIG. 12A
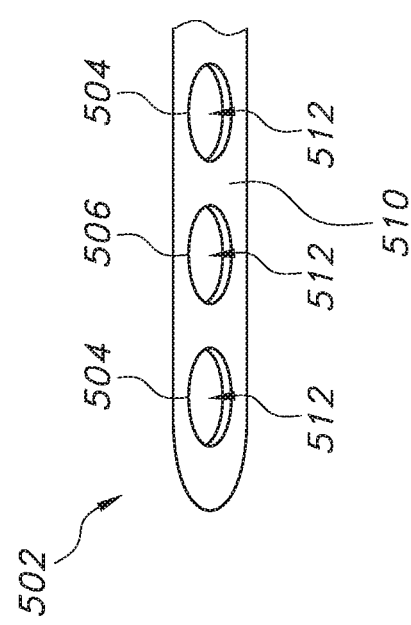
FIG. 12B
FIG. 13

ARTICLE AND METHOD FOR TREATING DIABETIC PERIPHERAL NEUROPATHY

RELATED APPLICATION

The present application is the national stage entry of International Patent Application No. PCT/US2017/065243, having a filing date of Dec. 8, 2017, which claims priority to U.S. Provisional Application Ser. No. 62/439,283, filed on Dec. 27, 2016, both of which are incorporated herein in their entirety by reference thereto.

FIELD OF THE INVENTION

The present invention relates to articles, systems, and methods for treating, nerve damage, loss of normal sensation and pain associated with nerve dysfunction such as found in, but not limited to, diabetic peripheral neuropathy (DPN), by repairing or restoring blood flow or perfusion to nervous tissues via electrical stimulation or neuromodulation.

BACKGROUND

Diabetes is an illness responsible for many associated debilitating medical conditions that have an increasing impact both socially and economically across the globe. A number of these conditions that are associated with diabetes in a dysregulation of small blood vessels of the vascular system that maintain a normal blood perfusion to such tissues as the retina in the eye, the glomerulus in the kidney and the peripheral nervous system. When the peripheral nerves become starved of normal blood supply as is found in diabetes, these nerves become dysfunctional and the clinical result is DPN where normal sensation in the periphery is lost with chronic pain being a component along with loss of sensation/numbness, paresthesia (e.g., tingling or "pins and needles" feeling). Diabetic peripheral neuropathy affects about 50% of the people diagnosed with diabetes. In 2014, 387 million people were living with diabetes in the world, and it is estimated that by 2035, 592 million people globally will have diabetes. Thus, it is estimated that about 194 million people suffer from diabetic peripheral neuropathy, and that by 2035, 296 million people will suffer from diabetic peripheral neuropathy globally. The instigator of the small blood vessel damage that is associated with diabetes that is responsible for DPN is the high circulating glucose concentration that is the hallmark of the diabetes. Glucose is toxic to blood vessels and in DPN the result of this is often observed as arterial attenuation and venous tortuosity around critical nerves in the periphery, such as the sural nerve in the lower leg that is associated with a sensory field in the foot. Patients experiencing DPN are often unable to sense normal environment feedback and the result often is injury to feet or hands which go on to heal poorly because of poor small vessel circulation, ulceration and infection. Chronic pain and amputations are commonplace in DPN. Currently available treatments include lifestyle modifications, weight loss programs and other treatments directed only at temporary symptomatic relief of pain such as transcutaneous electrical stimulation (TENS) and drug treatment. The medications used to treat DPN are often opioids, anti-seizure drugs, or antidepressants that often have intolerable side effects and low effectiveness, along with the risk of addiction. Further, none of the currently available treatments for DPN address the cause of the symptoms, which is diminished blood supply to the peripheral nerves.

As such, there remains a need for a safe, effective, and non-invasive method to increase blood flow and or perfusion of the peripheral nerves to repair nerve tissue, restore normal sensation in the periphery and to treat the pain associated with DPN.

SUMMARY

The problems discussed above are addressed by the present invention, which encompasses an article and method for treating peripheral neuropathy by restoring blood flow to target nerve tissue in a non-invasive manner. For instance, in one particular embodiment, the present invention is directed to an article for transcutaneously applying an appropriately contoured electrical stimulation to target nerve tissue to treat a patient having peripheral neuropathy. The article includes a support on which at least one electrode pair is positioned; a pulse generator attached to the at least one electrode pair via one or more leads; and a power supply connected to the pulse generator. The article is configured to deliver electrical stimulation to the target nerve tissue via the at least one electrode pair at a level sufficient to initiate vasodilation of vasculature within or adjacent the target nerve tissue, wherein the vasculature is responsible for perfusing the target nerve tissue with blood.

In one embodiment, the power supply can be connected to the support.

In another embodiment, the support is a wrap, a sock, a glove, or a finger cot. Further, the wrap, the sock, the glove or the finger cot can be constructed from a molded material, or the wrap, the sock, the glove, or the finger cot can be constructed from a nonwoven material.

In still another embodiment, the peripheral neuropathy that is being treated can be diabetic peripheral neuropathy.

In yet another embodiment, the target nerve tissue can be located within or adjacent a peripheral nerve.

In one particular embodiment, the target nerve tissue can be located in a foot, a hand, a distal phalanx of a toe, a distal phalanx of a finger, or a combination thereof.

In an additional embodiment, the vasculature can include a resistance-sized blood vessel having a lumen diameter of less than about 400 micrometers.

In one more embodiment, the article can relieve pain caused by the peripheral neuropathy.

In yet another embodiment, the article can facilitate recovery of a loss of sensation resulting from the peripheral neuropathy.

In another embodiment, the article can be configured to deliver the electrical field stimulation at a frequency ranging from about 0.1 Hertz to about 200 Hertz.

In still another embodiment, the article can be configured to deliver the electrical field stimulation at a current ranging from about 0.1 milliamps to about 60 milliamps.

In yet another embodiment, the article can be configured to deliver the electrical field stimulation at a voltage ranging from about 0.1 volts to about 200 volts.

In one more embodiment, the article can be configured to deliver the electrical field stimulation as a series of pulses each having a pulse width ranging from about 0.1 milliseconds to about 250 milliseconds.

In one particular embodiment, the present invention is also directed to a method for transcutaneously applying electrical stimulation to target nerve tissue to treat a patient having peripheral neuropathy. The method includes positioning at least one electrode pair adjacent an area of skin overlying the target nerve tissue; and delivering electrical stimulation to the target nerve tissue via the at least one electrode pair. The electrical stimulation is delivered at a level sufficient to initiate vasodilation of vasculature within or adjacent the target nerve tissue, wherein the vasculature is responsible for perfusing the target nerve tissue with blood.

In one embodiment, the at least one electrode pair can be positioned on a support.

In another embodiment, the support can be a wrap, a sock, a glove, or a finger cot. Further, the wrap, the sock, the glove, or the finger cot can be constructed from a molded material or the wrap, the sock, the glove, or the finger cot can be constructed from a nonwoven material.

In still another embodiment, the peripheral neuropathy can be diabetic peripheral neuropathy.

In yet another embodiment, the target nerve tissue can be located within or adjacent a peripheral nerve.

In an additional embodiment, the target nerve tissue can be located in a foot, a hand, a distal phalanx of a toe, a distal phalanx of a finger, or a combination thereof.

In one more embodiment, the vasculature can include a resistance-sized blood vessel having a lumen diameter of less than about 400 micrometers.

In another embodiment, the method can restore normal sensation caused by the peripheral neuropathy.

In yet another embodiment, the method can relieve pain caused by the peripheral neuropathy.

In an additional embodiment, the method can facilitate recovery of a loss of sensation resulting from the peripheral neuropathy.

In still another embodiment, the electrical stimulation can be delivered at a frequency ranging from about 0.1 Hertz to about 200 Hertz.

In yet another embodiment, the electrical stimulation can be delivered at a current ranging from about 0.1 milliamps to about 60 milliamps.

In an additional embodiment, the electrical stimulation can be delivered at a voltage ranging from about 0.1 volts to about 200 volts.

In another embodiment, the electrical stimulation can be delivered as a series of pulses each having a pulse width ranging from about 0.1 milliseconds to about 250 milliseconds.

The present invention is also directed to a system for percutaneously applying electrical stimulation to target nerve tissue to treat a patient having peripheral neuropathy. The system includes a percutaneous electrode assembly; an implantable pulse generator attached to the percutaneous electrode assembly via one or more leads; and a power supply for supplying power to the implantable pulse generator, wherein the article is configured to deliver electrical field stimulation to the target nerve tissue via the percutaneous electrode assembly at a level sufficient to initiate vasodilation of vasculature adjacent the target nerve tissue, wherein the vasculature is responsible for perfusing the target nerve tissue.

In one embodiment, the peripheral neuropathy can be diabetic peripheral neuropathy.

In another embodiment, the target nerve tissue can be located within or adjacent a peripheral nerve.

In an additional embodiment, the target nerve tissue can be located within a foot, a hand, a distal phalanx of a toe, a distal phalanx of a finger, or a combination thereof.

In still another embodiment, the vasculature can include a resistance-sized blood vessel having a lumen diameter of less than about 400 micrometers.

In yet another embodiment, the system can relieve pain caused by the peripheral neuropathy.

In one more embodiment, the system can facilitate recovery of a loss of sensation resulting from the peripheral neuropathy In one particular embodiment, the system can be configured to deliver the electrical stimulation at a frequency ranging from about 0.1 Hertz to about 200 Hertz.

In another embodiment, the system can be configured to deliver the electrical stimulation at a current ranging from about 0.1 milliamps to about 60 milliamps.

In an additional embodiment, the system can be configured to deliver the electrical stimulation at a voltage ranging from about 0.1 volts to about 200 volts.

In still another embodiment, the system can be configured to deliver the electrical stimulation as a series of pulses each having a pulse width ranging from about 0.1 milliseconds to about 250 milliseconds.

The present invention is also directed to a method for percutaneously applying electrical stimulation to target nerve tissue to treat a patient having peripheral neuropathy. The method includes positioning a percutaneous electrode assembly adjacent an area of skin overlying the target nerve tissue; and delivering electrical stimulation to the target nerve tissue via the percutaneous electrode assembly, wherein the electrical stimulation is delivered at a level sufficient to initiate vasodilation of vasculature within or adjacent the target nerve tissue, wherein the vasculature is responsible for perfusing the target nerve tissue.

In one embodiment, the peripheral neuropathy can be diabetic peripheral neuropathy.

In another embodiment, the target nerve tissue can be located within or adjacent a peripheral nerve.

In an additional embodiment, the target nerve tissue can be located within a foot, a hand, a distal phalanx of a toe, a distal phalanx of a finger, or a combination thereof.

In still another embodiment, the vasculature can include a resistance-sized blood vessel having a lumen diameter of less than about 400 micrometers.

In yet another embodiment, the method can relieve pain caused by the peripheral neuropathy.

In one more embodiment, the method can facilitate recovery of a loss of sensation resulting from the peripheral neuropathy.

In one particular embodiment, the electrical stimulation can be delivered at a frequency ranging from about 0.1 Hertz to about 200 Hertz.

In an additional embodiment, the electrical stimulation can be delivered at a current ranging from about 0.1 milliamps to about 60 milliamps.

In another embodiment, the electrical stimulation can be delivered at a voltage ranging from about 0.1 volts to about 200 volts.

In yet another embodiment, the electrical stimulation can be delivered as a series of pulses each having a pulse width ranging from about 0.1 milliseconds to about 250 milliseconds.

These and other aspects of the present disclosure will become apparent upon reference to the following detailed description.

BRIEF DESCRIPTION OF THE DRAWINGS

The foregoing and other features and aspects of the present invention and the manner of attaining them will become more apparent, and the invention itself will be better understood by reference to the following description, appended claims and accompanying drawings, where:

FIG. 11 is a side perspective view of an exemplary percutaneous electrode assembly contemplated by the present invention;

FIGS. 12A and 12B are side perspective views of exemplary percutaneous electrode assemblies contemplated by the present invention in which an anode and cathode are present on only a portion of the radial surface of the electrode; and FIG. 13 is a side cross-sectional view of an exemplary percutaneous electrode assembly including a lumen or passageway for delivering fluid therethrough, as contemplated by the present invention.

Figure 1:
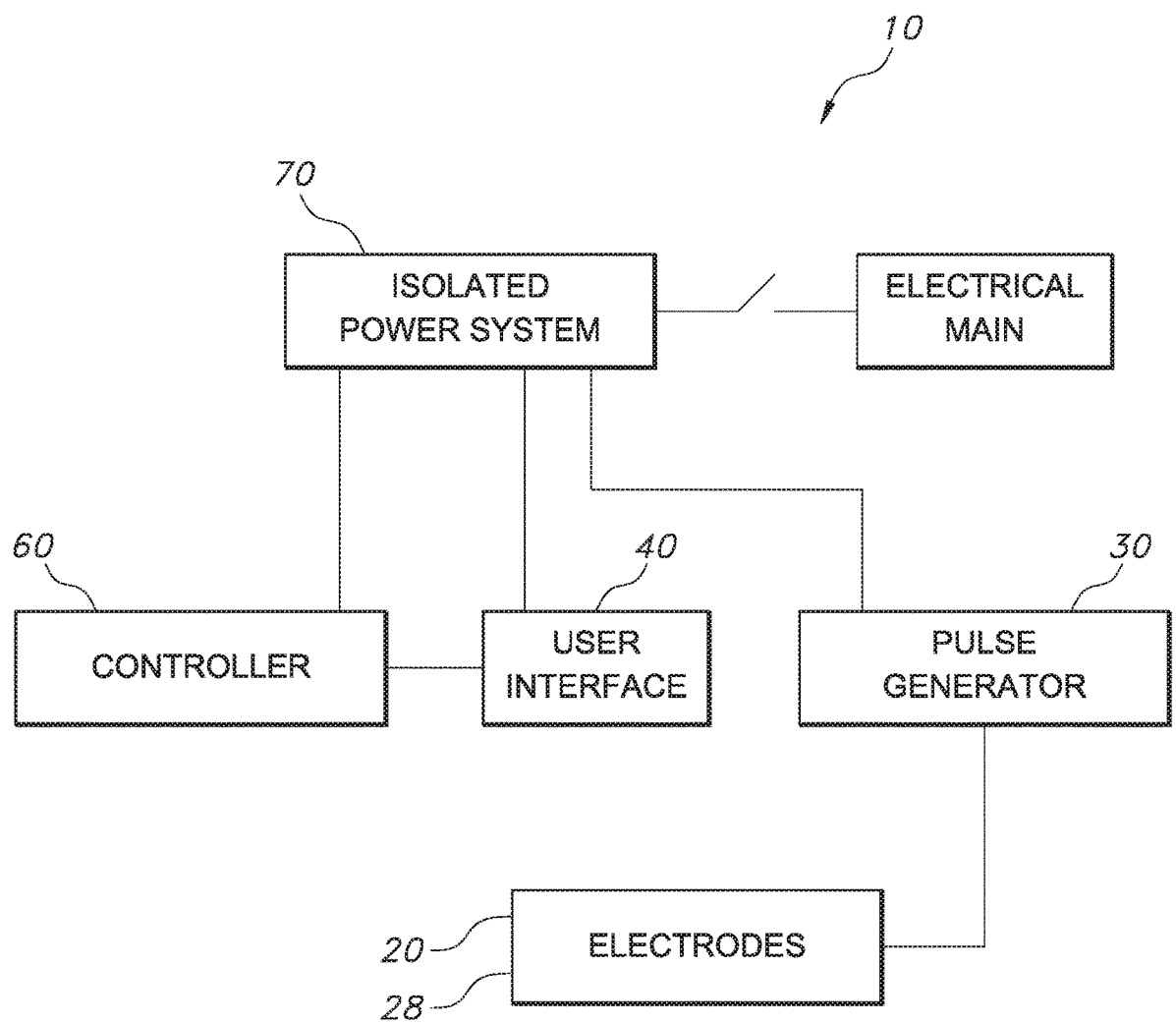
FIG. 1 is a schematic of the stimulation system contemplated by the present invention.

Repeat use of reference characters in the present specification and drawings is intended to represent same or analogous features or elements of the invention.

DETAILED DESCRIPTION

Reference now will be made in detail to various embodiments of the disclosure, one or more examples of which are set forth below. Each example is provided by way of explanation, not limitation of the disclosure. In fact, it will be apparent to those skilled in the art that various modifications and variations may be made in the present disclosure without departing from the scope or spirit of the invention. For instance, features illustrated or described as part of one embodiment, may be used on another embodiment to yield a still further embodiment. Thus, it is intended that the present invention cover such modifications and variations.

Generally speaking, an article and method for non-invasively treating peripheral neuropathy in a patient via transcutaneous stimulation of target nerve tissue are contemplated by the present invention. For instance, in one particular embodiment, the article of the present invention includes a support on which at least one electrode pair is positioned; a controller attached to the at least one electrode pair via one or more leads; and a power supply connected to the controller. The article is configured to deliver electrical stimulation to the target nerve tissue via the at least one electrode pair at a level sufficient to initiate vasodilation of vasculature adjacent the target nerve tissue. Meanwhile, in another embodiment, the method of the present invention includes positioning at least one electrode pair adjacent an area of skin overlying the target nerve tissue; and delivering electrical stimulation to the target nerve tissue via the at least one electrode pair, where the electrical stimulation is delivered with an appropriate contour and at a level sufficient to initiate vasodilation of vasculature within or adjacent the target nerve tissue and responsible for perfusion of the target nerve tissue. An implantable system and method for treating peripheral neuropathy via percutaneous electrical stimulation are also contemplated by the present invention.

Without intending to be limited by any particular theory, the present inventors have discovered that selectively controlling the electrical stimulation parameters applied transcutaneously or percutaneously to target nerve tissue (e.g., sensory nerves), where the target nerve tissue is a source of pain and loss of sensation related to DPN, can facilitate dilation of the arterial vasculature within or adjacent the target nerve tissue. This, in turn, results in increased blood flow to or perfusion of the target nerve tissue, which reduces the pain and paresthesia associated with damage to the target nerve tissue. For instance, stimulation of the target nerve tissue can promote the release of the vasodilator calcitonin gene-related peptide (CGRP), which can increase blood flow in the vasculature adjacent the target nerve tissue. Further, it is also believed that stimulation of the target nerve tissue can increase production of the vasodilator nitric oxide (NO) from the endothelium of the vasculature, which can also increase blood flow in the vasculature within or adjacent or within the target nerve tissue by relaxing the smooth muscle cells and increasing the diameter of the vasculature.

Moreover, although treatment of DPN is described in detail herein, the systems and methods of the present invention are also contemplated for use in the treatment of peripheral neuropathy associated with other diseases or conditions besides diabetes. For example, in addition to diabetes, other diseases or conditions that cause peripheral neuropathy include, but are not limited to: nerve compression, entrapment or laceration (e.g., crutches, ulnar neuropathy, thoracic outlet syndrome, meralgia paresthetica, Morton's metatarsalgia); other metabolic disorders (e.g., hypothyroidism); autoimmune disorders (e.g., lupus, rheumatoid arthritis, Guillain-Barre Syndrome, Miller Fisher Syndrome); kidney disease, liver disease, toxin-induced neuropathy (e.g., related to alcohol, tobacco, asbestos, arsenic, lead, or mercury); malignant lymphoma; lung cancer; viral or bacterial infections (e.g., HIV, Lyme disease, leprosy, poliomyelitis); medication-induced neuropathy (chemotherapy); trauma; carpal tunnel syndrome; cubital tunnel syndrome; and vitamin deficiency (e.g., vitamin B deficiency). Inherited causes of peripheral neuropathy include Charcot-Marie Tooth disease, Kennedy's disease (X-linked bilbospinal muscular atrophy), Van Allen's Syndrome (hereditary amyloid neuropathy), Refsum's disease, and Tangier disease. Various embodiments of the systems and methods for treating peripheral neuropathy associated with such diseases and conditions are described in more detail below.

In one embodiment, an article and method of the present invention contemplates non-invasively treating pain associated with a peripheral nerve disease such as DPN via transcutaneous electrical stimulation of target nerve tissue in a patient, where the target nerve tissue is a source of the patient's pain. The target nerve tissue can include peripheral nerves that have been damaged due to lack of blood flow to the target nerve tissue. The lack of blood flow leads to endoneurial hypoxia, which in turn impairs nerve metabolism and leads to the pain and numbness associated with DPN. The lack of blood flow can be caused by arterial attenuation, vascular tortuosity, inflammation, or a combination thereof, which can be the result of endothelial cell proliferation, basement membrane thickening, increased diffusion distance, epineurial arterio-venous shunting, hyper-reactive platelets, elevated blood viscosity, erythrocyte rigidity, etc., each of which can be associated with diabetes. The electrical stimulation can be in the form of specifically controlled and contoured waveforms that facilitate energy-dependent vasodilation of the vasculature within or adjacent the target nerve tissue, thus increasing blood flow to or perfusion of to the target nerve tissue, which, in turn, can relieve pain and restore sensation to the patient.

As shown in FIG. 1, the present invention contemplates the use of a stimulation system 10 that can include a pulse generator 30, a user interface 40, a controller 60, and an isolated power system 70. The stimulation system 10 can be connected to an article via electrodes (at least one cathode 20 and at least one anode 28) using electrical leads 31 (see FIGS. 2-9), where the electrodes deliver transcutaneous electrical stimulation from the pulse generator 30 to the target nerve tissue affected by DPN. As discussed in more detail with respect to FIGS. 2-9, the electrodes can be positioned on a support 50 (e.g. a sock 80, a glove 90, a finger cot 96, or a wrap 97 or 98) to deliver electrical stimulation to target nerve tissue in a desired location (e.g., ankles, feet, toes, wrists, hands, fingers, etc.). In addition, as shown in FIG. 10, the present invention also contemplates a system that is implantable and can deliver percutaneous electrical stimulation to target nerve tissue. Further, while an experimental-scale system is shown and described, it is contemplated that a more compact unit could be used to control and deliver the desired electrical stimulation. Further, in some embodiments, the system can be portable and user-friendly such that a patient can utilize the system at home, outside of a medical office setting. However, it is also to be understood that the system can also be used in a medical office setting.

Whether the system is transcutaneous or percutaneous, at least two electrodes 20, 28 (i.e., an electrode pair) are generally needed to deliver electrical stimulation to target nerve tissue via contoured waveforms selectively controlled to facilitate dilation of the vasculature adjacent the target nerve tissue. The cathode 20 or stimulating electrode delivers a positive-going pulse that attracts negatively-charged ions, while the anode 28 or ground electrode delivers a negative-going pulse that attracts positively-charged ions. The movement of ions within the tissue approximates a current flow and likely acts on sensory receptors in the target nerve tissue by modulating their receptor potential and sensitizing the organ. The electrodes 20 and 28 (described herein) are attached to insulated leads 31 that pass to pulse generator 30.

In some embodiments, the electrodes 20, 28 can be made from a variety of conductive materials. Such materials include carbon, metals (e.g., platinum, palladium, gold, tungsten, titanium, etc.), metal-based compounds (e.g., oxides, chlorides, etc.), metal alloys, conductive polymers, or a combination thereof. Particular examples of carbon electrodes include glassy carbon, graphite, mesoporous carbon, nanocarbon tubes, fullerenes, etc.

The electrodes 20, 28 may be in the form of a film. Thin films of the conductive materials may be formed by a variety of methods including, sputtering, reactive sputtering, physical vapor deposition, plasma deposition, chemical vapor deposition (CVD), printing, spraying, and other coating methods. For instance, carbon or metal-paste based conductive materials can be formed using screen printing. Metal-based electrodes can be made using standard sputtering or CVD techniques. In other aspects, the electrodes 20, 28 can be formed by stamping or cutting thin sheets of desired metals as is known in the art.

Each electrode 20, 28 can be unique in shape and size, or the electrodes may be identical in shape and size. Any variety of shapes can be used (e.g. rectangle, circle, oval, random, etc.) The size of an electrode 20, 28 can be determined by the available skin contact or surface area. In general, larger electrodes will enable larger areas of sensitization.

In one aspect of the present invention, the electrodes 20, 28 can be screen printed onto a support 50 (e.g., a sock 80, a glove 90, a finger cot 96, a wrap 97 or 98, etc.). The electrodes 20, 28 can be made with a carbon paste and polymeric binder, which are mixed together with a volatile solvent to create a screen printable "ink." The resulting thickness of the screen printed electrodes (once the volatile has evaporated) can range from about 0.25 microns to about 100 microns, such as from about 0.5 microns to about 50 microns, such as from about 0.75 microns to about 20 microns, such as from about 1 micron to about 10 microns. These thicknesses are also contemplated for the other aforementioned types of electrodes 20, 28 that can alternatively be employed.

In another aspect of the present invention, the electrodes 20, 28 may be constructed from woven or nonwoven threads made from conductive fibers. The threads may have a round or rectangular cross-section and may have the same thickness as described above for the screen printed electrodes. The threads may be woven into the material from which a support 50 (e.g., a sock 80, a glove 90, a finger cot 96, a wrap 97 or 98, etc.) is made.

In yet another alternative, the electrodes 20, 28 may have a laminate structure. Again, such electrodes have the same thickness as the screen printed electrodes. In still another alternative, the electrodes 20, 28 may be in the form of a nerve cuff, such as in the embodiment contemplated by FIG. 10 where the electrodes are implantable to provide for the delivery of percutaneous electrical nerve stimulation.

Regardless of their particular form, the electrodes 20, 28 are positioned on a support 50 such that they can come into contact with a patient's skin, and the electrodes 20, 28 are also connected to a pulse generator 30 via one or more leads 31. The leads 31 conduct electricity from the pulse generator 30 to the electrodes 20, 28 as determined via parameters input into the controller 60, and can be made from a material that is the same or different than the material of the electrodes 20, 28.

In one aspect, the leads 31 can be screen printed onto a support 50. Such leads 31 can be made from a composition that includes silver or a silver chloride paste as well as a polymeric binder. Volatile solvents can be added to this composition to create an "ink" that can be screen printed either over the top of the previously printed carbon leads, or in place of the carbon leads. The resulting thickness of the screen printed leads (once the volatile has evaporated) can range from about 0.25 microns to about 100 microns, such as from about 0.5 microns to about 50 microns, such as from about 0.75 microns to about 20 microns, such as from about 1 micron to about 10 microns.

The leads 31 can also be electrically insulated so that they do not short in the presence of moisture. If the leads 31 are screen printed leads, an insulation coating is placed over the top of the lead, creating a seal between the support immediately surrounding the lead and the coating. If the leads 31 are threads or laminate strips, the entire thread/strip may be coated with insulation material prior to placement onto the support of before integration therewith.

In one aspect, the leads 31 can be coated with a photoresist material such as an organic compound that can be altered by exposure to light of a particular wavelength or range of wavelengths. An exemplary coating technique includes depositing a layer of a photoresist over the leads 31. Exposure to light makes the photoresist material less susceptible to removal by chemical agents. After the layer of photoresist material is applied, it is exposed to light, or other electromagnetic radiation, through a mask.

Referring now to FIGS. 2-9, a support 50 such as a glove 80, a sock 90, a finger cot 96, a foot wrap 97, or a hand wrap 98 are exemplary articles to which the electrodes 28, 30 may be attached (e.g. adhesively or mechanically) or even integrated (e.g., a wrap, a woven sock, or a glove made with conductive and non-conductive threads or a film-like finger cot 96 made with embedded electrodes) for use with the stimulation system 10 discussed above. These articles can be molded from a polymeric material, a woven material, a nonwoven material, or a combination thereof.

Molded socks, gloves, finger cots, or wraps may be made by conventional methods known in the art, such as by dipping, spraying or otherwise coating a mold with a desired material and turning the article inside out after placement of the electrodes 28, 30 and curing the material (not necessarily in that order). For example, socks 80, gloves 90, or wraps 97 or 98 may be made in a manner as described in U.S. Pat. No. 4,521,365 issued to Kurtz et al. or by U.S. Pat. No. 5,693,401 issued to Sommers, both of which are incorporated herein by reference to the extent they are consistent with the present disclosure.

In one particular embodiment, a support 50 can be in the shape of a sock 80, a glove 90, a finger cot 96, a foot wrap 97, or a hand wrap 98 that is molded from nitrile, acrylic, or latex. Because these materials are flexible and elastic, the leads 31 attached to these materials may necessarily be flexible as well. Elasticity may not be inherent to the materials to which the leads 31 are made. Thus, to create pseudo-elasticity in what might be a non-elastic material, the lead 31 may be applied to the support surface in a sawtooth or sinusoidal pattern (not shown).

One advantage of an elastomeric sock 80, glove 90, finger cot 96, foot wrap 97, or hand wrap 98 is that it can be fit to a person's foot, hand, or finger in a way that creates constant pressure. This makes the electrode 20, 28 contact with a patient's skin constant, which is greatly desired to ensure that the desired electrical field stimulation is delivered to the target nerve tissue. In one aspect, the sock 80, glove 90, finger cot 96, foot wrap 97, or hand wrap 98 is sufficiently elastic so that when attached to the user's body, it is capable of applying forces upon the body tissue and compliantly responding to force resultant from body motion.

In one aspect, a coupling media such as an electrically conductive gel or paste may be applied to a surface of the electrodes 20, 28 to enhance the conductivity of the skin and/or lower impedance. Desirably, the electrolytic gel or paste can coat a skin-facing surface of the electrodes 20, 28 so that the gel or paste enhances the contact between the patient's skin and the electrodes 20, 28. Examples of conductive pastes include TEN20 conductive paste from Weaver and Company, Aurora, Colo., and ELEFIX Conductive Paste from Nihon Kohden with offices at Foothill Ranch, Calif. Examples of conductive gels include SPECTRA 360 Electrode Gel from Parker Laboratories, Inc., Fairfield, N.J., or ELECTRO-GEL from Electro-Cap International, Inc., Eaton, Ohio.

In another aspect, the sock 80, glove 90, finger cot 96, foot wrap 97, or hand wrap 98 may be made from a woven material. A woven structure provides the opportunity to weave insulated leads into very fabric from which these articles are constructed. Because the leads 31 are not elastomeric, the selected weave is such that when an appendage in a sock 80, glove 90, finger cot 96, foot wrap 97, or hand wrap 98 moves, the resulting tensile or compressive forces do not cause the lead 31 to fail mechanically. Thus, a knitted fabric may be more desirable than a flat-weave fabric as many knitted weave patterns can stretch even when the threads used to make the fabric are not elastomeric. However, a flat-weave fabric (or knitted fabric) of conductive materials may have leads 31 stitched or glued thereon in a pattern that can accommodate tensile or compressive forces.

A thread or yarn making up the majority of a fabric used to make the sock 80, glove 90, finger cot 96, foot wrap 97, or hand wrap 98 can be one or more non-conductive materials such as nylon, acrylic, wool, cotton, rayon or the like. These threads or yarns typically have round cross-sections with a diameter of about 0.25 millimeters to about 2 millimeters. These diameters may be quite different than the diameters of leads 31.

As mentioned above, the electrodes (cathode 20 and anode 28) may each be electrically connected via a lead 31 to the stimulation system 10. Specifically, the electrodes can be connected via lead 31 to a pulse generator 30. The pulse generator 30 can be a constant-current stimulator. One exemplary stimulator is the constant-current DIGITIMER DS5 peripheral electrical stimulator available from Digitimer Ltd., England. The DIGITIMER DS5 machine delivers a bipolar stimulation via a pair of electrodes (cathode 20 and anode 28), where both electrodes are within a specified distance from the target nerve tissue. In another aspect of the present disclosure, pulse generator 30 may be a constant-voltage pulse-generator. For example, three such generators are available from Grass Technologies, a subsidiary of Astro-Med, Inc., RI, US, as models S88X, S48, SD9. It should also be understood that monopolar stimulation, where just one electrode is placed within a specified distance from the target nerve tissue and a reference electrode is located elsewhere, will also activate a target nerve tissue and cause sensory nerve stimulation, but with lesser effectiveness.

The system 10 also includes a user interface 40, which is a computer that can operate software designed to record signals passed from the controller 60, and to drive the controller's output from the pulse generator 30. Possible software includes Cambridge Electronic Design's (UK) "SPIKE" program. The software is programmable and can record and analyze electrophysiological signals, as well as direct the controller 60 to enable electrical stimulation for treatment of a vascular disorder such as DPN.

Further, the controller 60 performs data acquisition functions by acquiring electrophysiological waveform data from, for instance, signal amplifiers/conditioners (not shown), and outputs electrical signals for real-time control of the pulse generator 30. The controller 60 may have onboard memory to facilitate high speed data capture, independent waveform sample rates and on-line analysis. In one aspect, the controller 60 may be a POWER 1401 data-acquisition interface unit available from Cambridge Electronic Design, UK.

The various components of the system 10 can be powered by an isolated power supply 70 to protect them from ground faults and power spikes carried by the electrical main. An exemplary isolated power supply is the Model IPS115 Isolated Medical-grade Power System from Grass Technologies, a subsidiary of Astro-Med, Inc., West Warwick, R.I., USA. Although not shown, the system 10 can also be powered by a battery so that the system can be portable. In one embodiment, the battery can be rechargeable.

Figure 2:
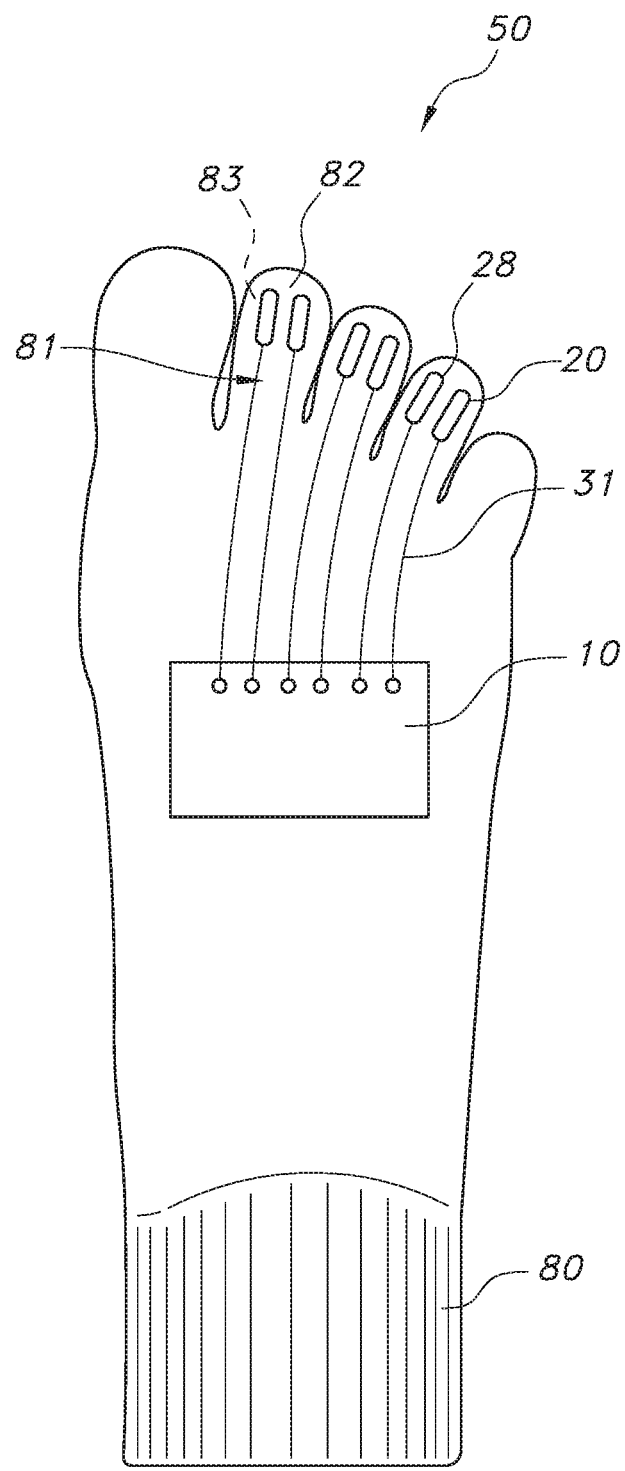
FIG. 2 is a top view of one embodiment of an article contemplated by the present invention, where the article is in the form of a sock.

Various articles that can be used in conjunction with the stimulation system 10 will now be discussed in more detail. Turning first to FIG. 2, an article that includes a support 50 in the form of a sock 80 is illustrated. Although the stimulation system 10 discussed above with respect to FIG. 1 is shown as being positioned on the sock 80, this is not necessarily required, and one or more components of the stimulation system 10 may be separate from the sock 80. As shown, the sock 80 includes pairs of electrodes 20 and 28 positioned on one or more toe regions of the sock 80. Specifically, the electrodes 20 and 28 are positioned along a distal phalanx 81 of a toe so that the electrodes 20 and 28 can make contact with a dorsal surface 82 of the toe. However, although not shown, it is also to be understood that, alternatively, the electrodes 20 and 28 can be positioned along a distal phalanx 81 of a toe so that the electrodes 20 and 28 can make contact with a plantar surface 83 of the toe.

Figure 3:
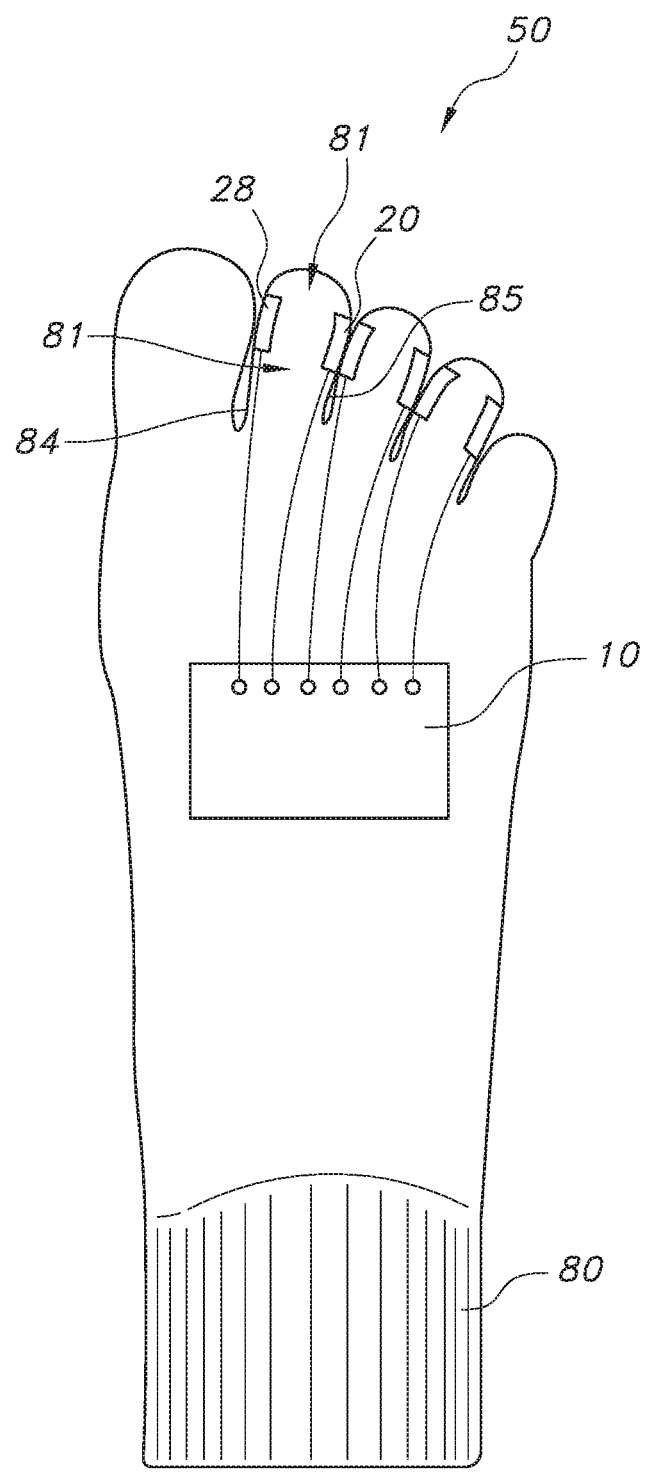
FIG. 3 is a top view of another embodiment of an article contemplated by the present invention, where the article is also in the form of a sock.

Next, in FIG. 3, another embodiment of an article that includes a support 50 in the form of a sock 80 is illustrated. Although the stimulation system 10 discussed above with respect to FIG. 1 is shown as being positioned on the sock 80, this is not necessarily required, and one or more components of the stimulation system 10 may be separate from the sock 80. As shown, the sock 80 includes pairs of electrodes 20 and 28 positioned on one or more toe regions of the sock 80. Specifically, the electrodes 20 and 28 are positioned along the distal phalanx 81 of a toe so that electrode 28 can make contact with a medial surface 84 of the toe and so that electrode 20 can make contact with a lateral surface 85 of the toe or vice versa (not shown).

Figure 4:
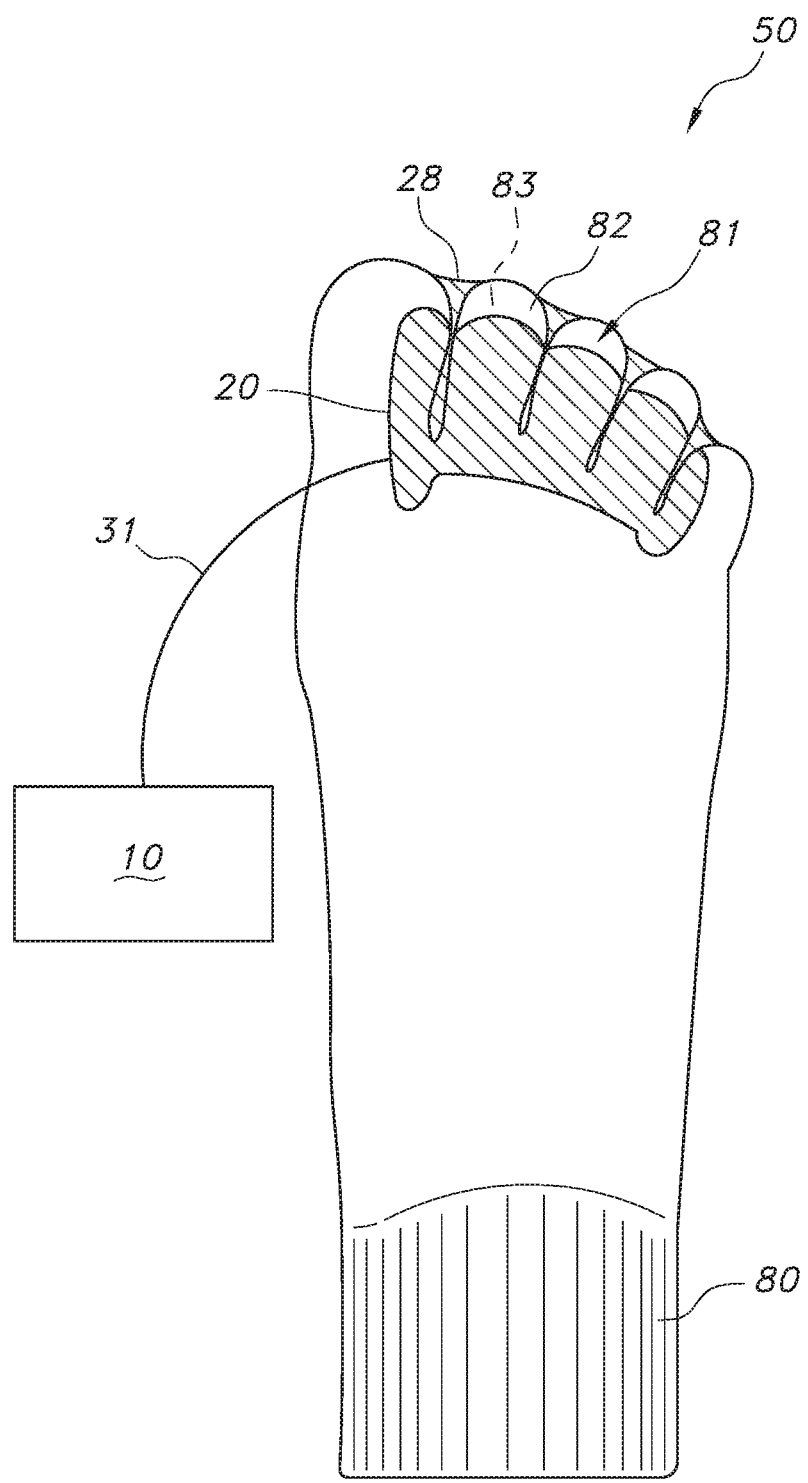
FIG. 4 is a top view of still another embodiment of an article contemplated by the present invention, where the article is also in the form of a sock.

Referring now to FIG. 4, one more embodiment of an article that includes a support 50 in the form of a sock 80 is illustrated. Although the stimulation system 10 discussed above with respect to FIG. 1 is shown as being positioned on the sock 80, this is not necessarily required, and one or more components of the stimulation system 10 may be separate from the sock 80. As shown, electrode 20 can be positioned along a distal phalanx 81 of each toe so that the electrode 20 makes contact with a dorsal surface 82 of each toe, while electrode 28 can be positioned along a distal phalanx 81 of each toe so that the electrode 28 makes contact with a plantar surface 83 of each toe, where the electrode configuration resembles a clamp or clip that can fit over, between and beneath the distal phalanx regions 81 of each toe.

Figure 5:
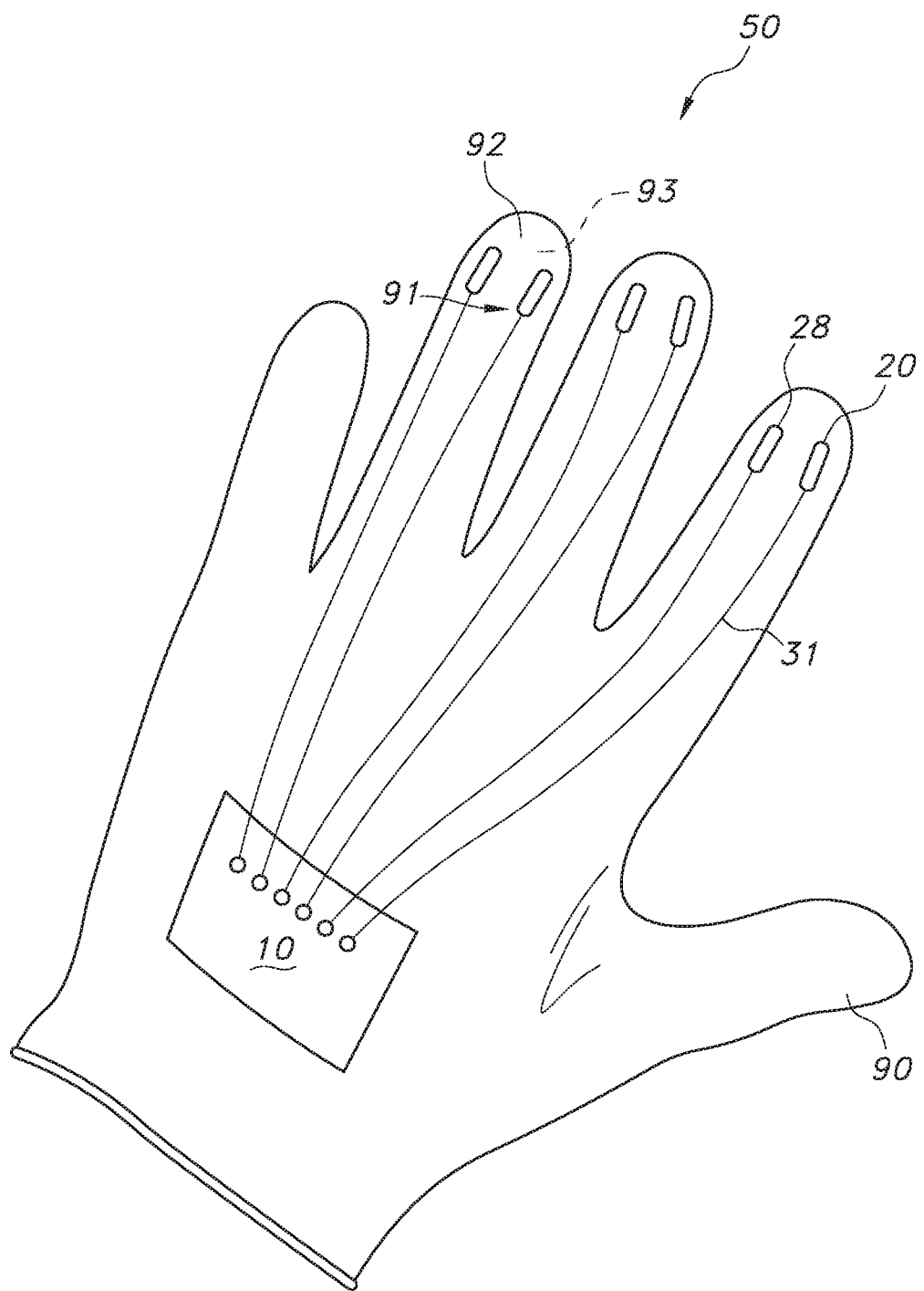
FIG. 5 is a top view of yet another embodiment of an article contemplated by the present invention, where the article is in the form of a glove.

In FIG. 5, an article that includes a support 50 in the form of a glove 90 is illustrated. Although the stimulation system 10 discussed above with respect to FIG. 1 is shown as being positioned on the glove 90, this is not necessarily required, and one or more components of the stimulation system 10 may be separate from the glove 90. As shown, the glove 90 includes pairs of electrodes 20 and 28 positioned on one or more finger regions of the glove 90. Specifically, the electrodes 20 and 28 are positioned along a distal phalanx 91 of a finger so that the electrodes 20 and 28 can make contact with a dorsal surface 92 of the finger. However, although not shown, it is also to be understood that, alternatively, the electrodes 20 and 28 can be positioned along a distal phalanx 91 of a finger so that the electrodes 20 and 28 can make contact with a palmar surface 93 of the finger. Alternatively, although not shown, one of the electrodes 20 can be positioned along a distal phalanx 91 of a finger so that the electrode 20 can make contact with a dorsal surface 92 of the finger, while the other electrode 28 can be positioned along a distal phalanx 91 of a finger so that the electrode 28 can make contact with a palmar surface 93 of the finger.

Figure 6:
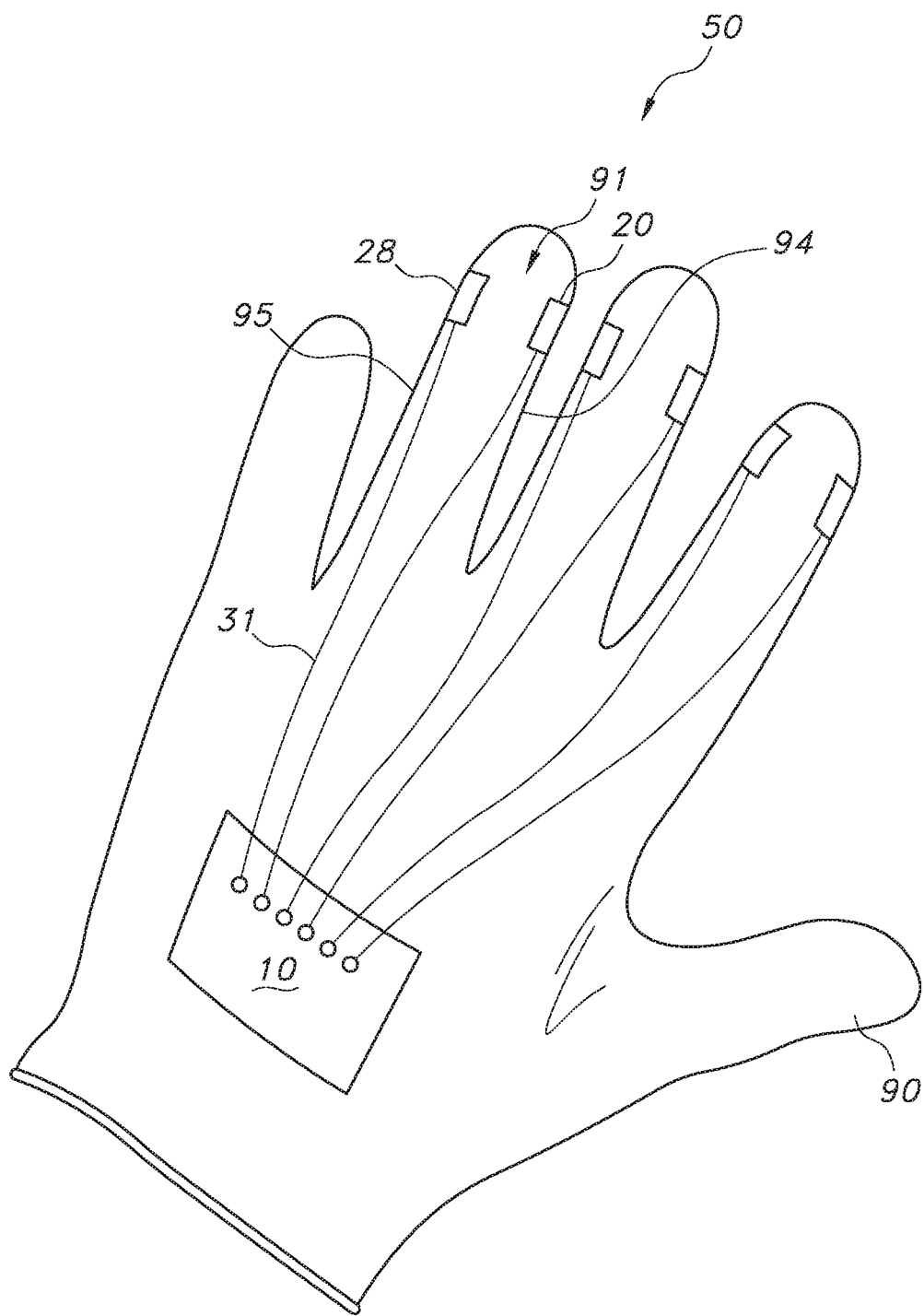
FIG. 6 is a top view of one more embodiment of an article contemplated by the present invention, where the article is also in the form of a glove.

Turning now to FIG. 6, an additional embodiment of an article that includes a support 50 in the form of a glove 90 is illustrated. Although the stimulation system 10 discussed above with respect to FIG. 1 is shown as being positioned on the glove 90, this is not necessarily required, and one or more components of the stimulation system 10 may be separate from the glove 90. As shown, the glove 90 includes pairs of electrodes 20 and 28 positioned on one or more finger regions of the glove 90. Specifically, the electrodes 20 and 28 are positioned along the distal phalanx 91 of a finger so that electrode 20 can make contact with a medial surface 94 of the finger and so that electrode 20 can make contact with a lateral surface 95 of the finger or vice versa (not shown).

Figure 7:
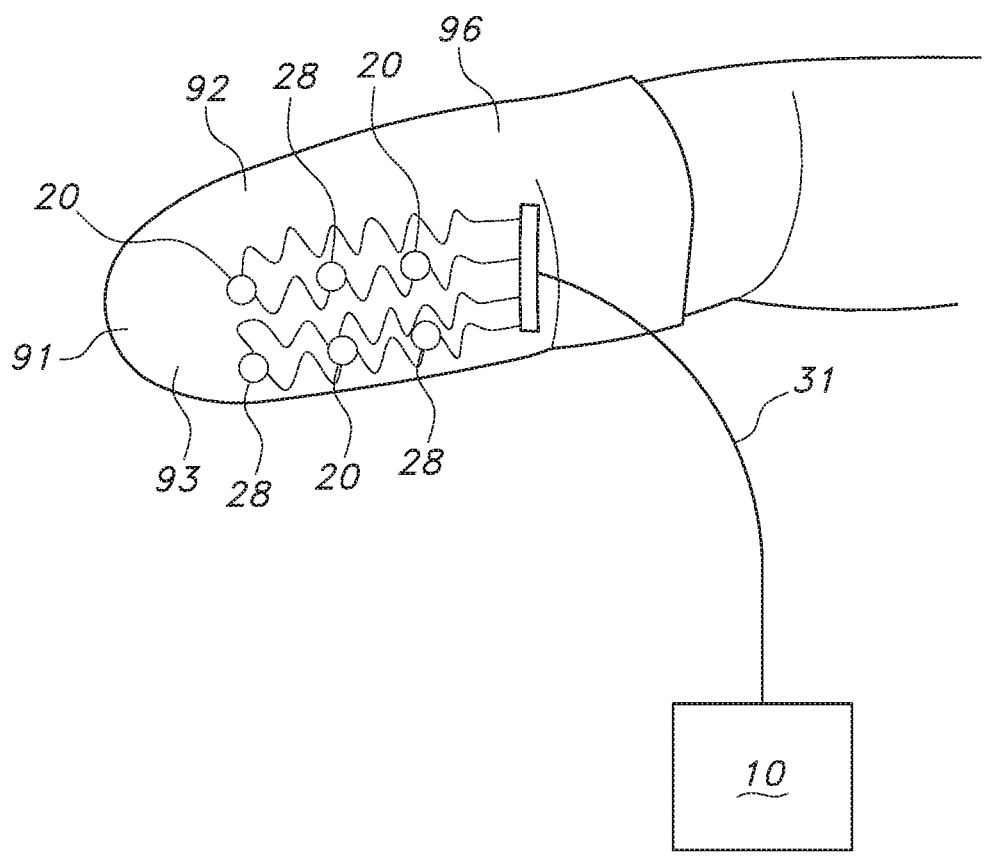
FIG. 7 is a top view of an additional embodiment of an article contemplated by the present invention, where the article is in the form of a finger cot.

Next, in FIG. 7, an article that includes a support 50 in the form of a finger cot 96 is illustrated. As shown, one or more components of the stimulation system 10 discussed above with respect to FIG. 1 may be separate from the finger cot 96. However, in some embodiments (not shown), one or more components of the stimulation system 10 may be positioned on the finger cot 96. Regardless of the exact arrangement of the stimulation system 10, the finger cot 96 can be positioned over the distal phalanx region 91 of a finger, where the finger cot 96 covers both the dorsal surface 92 and a palmar surface 93 of the finger. Multiple cathode electrodes 20 and anode electrodes 28 can be arranged along the finger cot 96 on the palmar surface 93 and connected to stimulation system 10 via one or more leads 31.

Figure 8:
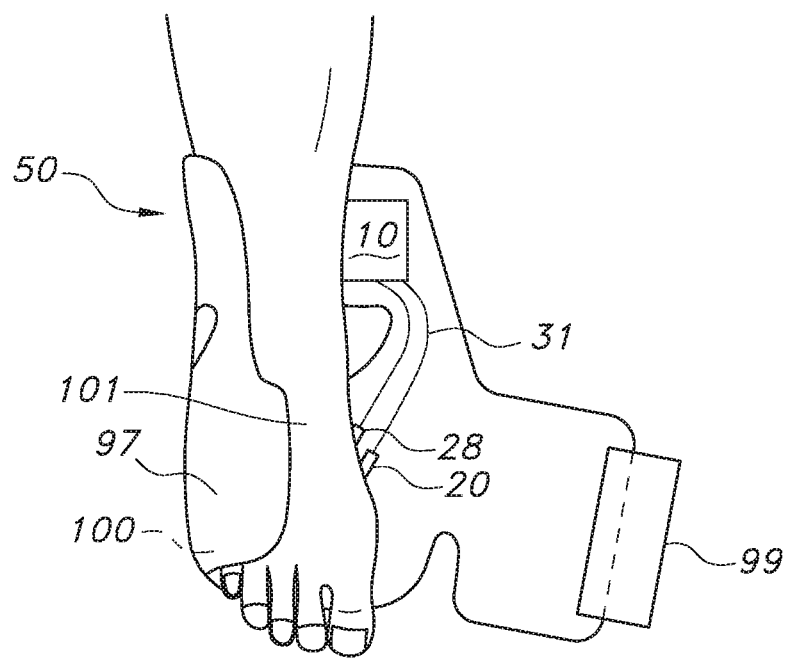
FIG. 8 is a side view of an additional embodiment of an article contemplated by the present invention, where the article is in the form of a foot wrap.

Referring now to FIG. 8, one more embodiment of an article that includes a support 50 in the form of a foot wrap 97 is illustrated. Although the stimulation system 10 discussed above with respect to FIG. 1 is shown as being positioned on the foot wrap 97, this is not necessarily required, and one or more components of the stimulation system 10 may be separate from the foot wrap 97. As shown, electrodes 20 and 28 can be positioned along a plantar surface 100 of the foot, and an attachment means 99 can be used to secure the foot wrap 97 at the dorsal surface 101 of the foot.

Figure 9:
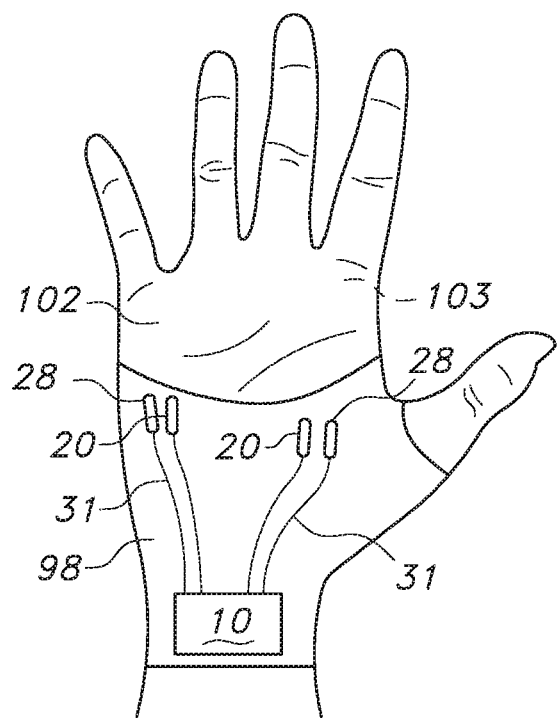
FIG. 9 is a side view of an additional embodiment of an article contemplated by the present invention, where the article is in the form of a hand wrap.
Figure 10:
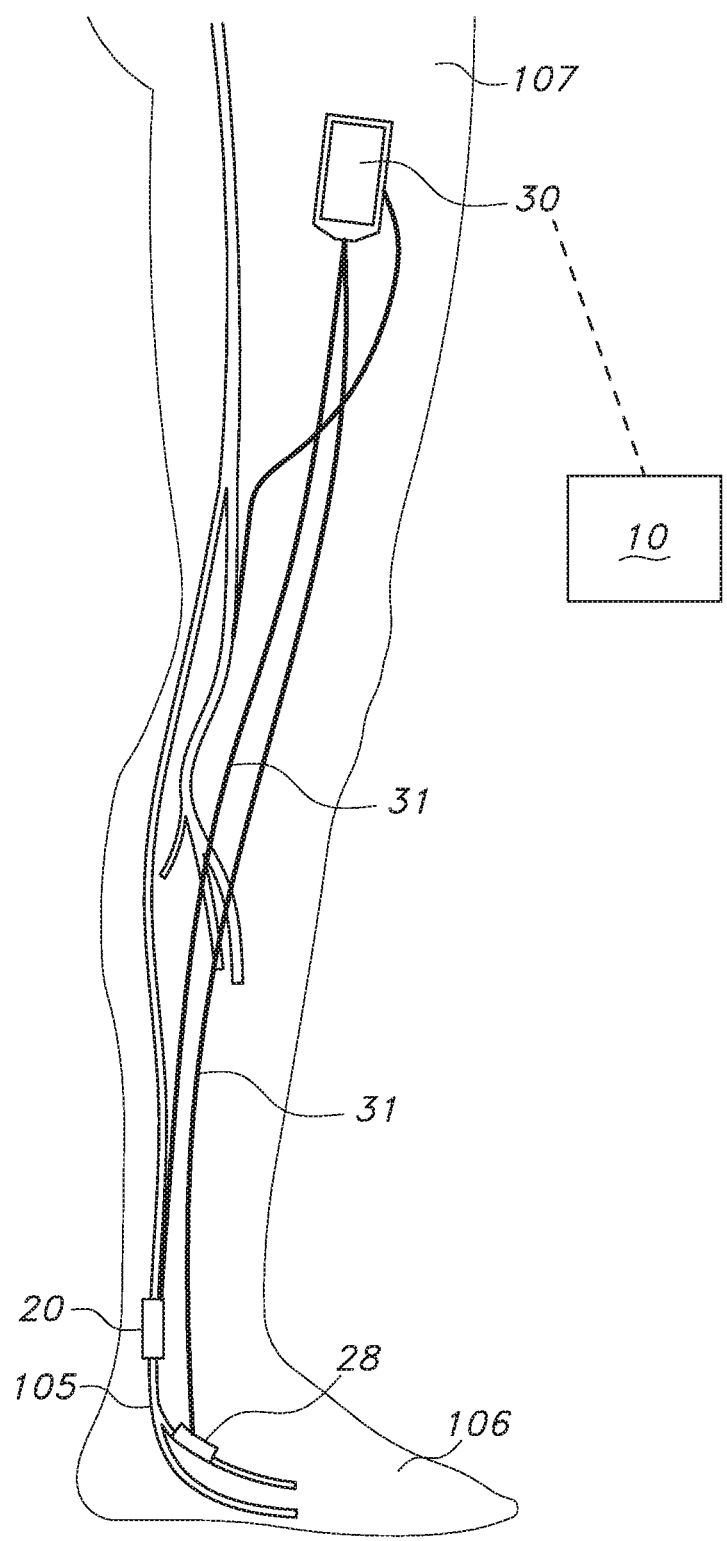
FIG. 10 is a perspective view of an additional embodiment of an article contemplated by the present invention, where the article is in the form of an implantable device.

In FIG. 9, an article that includes a support 50 in the form of a hand wrap 98 is illustrated. Although the stimulation system 10 discussed above with respect to FIG. 1 is shown as being positioned on the hand wrap 98, this is not necessarily required, and one or more components of the stimulation system 10 may be separate from the hand wrap 98. As shown, the hand wrap 98 includes pairs of electrodes 20 and 28 positioned on the wrap 98 so that the electrodes 20 and 28 can make contact with a palmar surface 102 of the hand. Although not shown, an attachment means can be used to secure the hand wrap 98 to the dorsal surface 103 of the hand.

Regardless of whether the transcutaneous electrical stimulation is being applied to target nerve tissue through electrodes positioned on or within a wrap, sock, glove, finger cot, etc. as discussed above, the electrical stimulation frequency for treatment of peripheral neuropathy (e.g., DPN) can range from about 0.1 Hertz to about 200 Hertz, such as from about 0.5 Hertz to about 175 Hertz, such as from about 1 Hertz to about 150 Hertz, such as from about 2.5 Hertz to about 130 Hertz. Such stimulation frequencies are sufficient to facilitate the vasodilation of vasculature (e.g., arteries and veins) adjacent the target nerve tissue which, in turn, increase blood flow to or perfusion of the target nerve tissue, resulting in a recovery of nerve function, sensation and reduction or elimination of the patient's pain due to peripheral neuropathy. In one particular embodiment, the vasculature includes resistance arteries, which are arteries that are generally less than about 400 micrometers in lumen diameter, which can include arteries having a lumen diameter ranging from about 100 micrometers to about 400 micrometers and arterioles having a lumen diameter of less than about 100 micrometers.

Further, the transcutaneous electrical stimulation can be applied at a current ranging from about 0.1 milliamps to about 60 milliamps, such as from about 0.5 milliamps to about 30 milliamps, such as from about 1 milliamp to about 15 milliamps, such as from about 1.5 milliamps to about 10 milliamps. Alternatively, the electrical stimulation can be applied at a voltage ranging from about 0.1 volts to about 200 volts, such as from about 1 volt to about 150 volts, such as from about 5 volts to about 125 volts, such as from about 10 volts to about 100 volts.

Moreover, each electrical stimulation pulse can have a pulse width ranging from about 0.1 milliseconds to about 250 milliseconds, such as from about 0.5 milliseconds to about 150 milliseconds, such as from about 1 millisecond to about 75 milliseconds, such as from about 2.5 milliseconds to about 25 milliseconds.

Further, although not required, in addition to an electrical stimulation (modulating) frequency, a carrier frequency can be utilized to improve energy transfer through the skin, so that electrical stimuli (current or voltage) can more easily and efficiently affect the target nerve tissue. The U.S. Food and Drug Administration recommends that power calculations for transcutaneous stimulation use a skin impedance of 500Ω. Studies show that the use of carrier frequencies up to 1 MHz can reduce the skin's impedance to 100Ω. As such, in some embodiments, the carrier frequency can range from about 25,000 Hertz to about 500,000 Hertz, such as from about 50,000 Hertz to about 300,000 Hertz, such as from about 100,000 Hertz to about 200,000 Hertz.

In addition to the transcutaneous system discussed above, as shown in FIG. 10, the present invention also contemplates a system that is implantable and can deliver percutaneous electrical stimulation to target nerve tissue, where vasculature affected by DPN is within or adjacent the target nerve tissue (e.g., the sural nerve). The stimulation system 10 of FIG. 10 is similar to that described with respect to FIGS. 2-9 except that the pulse generator 30, electrode leads 31, and electrodes 20 and 28 are implantable to enable the delivery of percutaneous electrical stimulation to the target nerve tissue 105 near a foot 106 or any other suitable location. Further, the implantable pulse generator 30, which can be implanted in an area near the thigh 107 or any other suitable location, is battery operated, where the battery used to power the pulse generator 30 can, in some embodiments, be rechargeable. Further, a wireless signal (as represented by the dashed line) enables communication between the implantable pulse generator 30 and the remainder of the system 10.

Referring generally to FIGS. 11 through 13 of the drawings, and more specifically to FIG. 11, there is illustrated in side perspective view an exemplary electrode assembly 502 that can be used for percutaneously delivering electrical stimulation directly to target nerve tissue instead of using the separate electrodes 20 and 28 that are shown in FIG. 10. The percutaneous electrode assembly 502 can be in the form of a percutaneous electrode or electrodes placed nearby the target nerve tissue. The percutaneous electrode assembly 502 used in a bipolar or multi-polar fashion can have an anode 504 and a cathode 506 placed nearby the target nerve tissue of interest. Monopolar percutaneous electrodes have a cathode 506 located nearby the target nerve tissue, and a return electrode (i.e., anode) positioned some distance away. Bipolar and multipolar electrode configurations have at least one cathode and one anode in the vicinity of the target nerve tissue. The electrode shape and size, and inter-electrode spacing are specific to contouring the electrical field surrounding the target nerve tissue, to enable vasodilation of the vasculature within or adjacent the target nerve tissue. For example, a suitable multipolar electrode may include a center cathode electrode 506 that is flanked by two anodes 504, where the anodal electrodes are connected together, effectively sharing a charge. The electrodes may be circumferential in shape (e.g., disposed radially at the surface of the electrode) and have a diameter ranging from 0.25 mm to 10 mm, and a width from 0.25 mm to 10 mm. For example, the electrodes may have a diameter ranging from about 0.25 mm to 5 mm, and a width from 0.25 mm to 5 mm. As another example, the electrodes may have a diameter ranging from about 0.25 mm to 3 mm, and a width from 0.25 mm to 3 mm. The inter-electrode spacing may have a range from 0.5 mm to 10 mm. Moreover, the electrodes may have varying impedances, to better contour the electric field that will facilitate the aforementioned vasodilation.

Referring now to FIG. 12A, there is illustrated a side perspective view of an exemplary percutaneous electrode assembly 502 for delivering percutaneous electrical stimulation directly to the vicinity of target nerve tissue to facilitate vasodilation of the vasculature within or adjacent the target nerve tissue in which an anode 504 and cathode 506 are present on only a portion of the radial surface of the electrode assembly 502. As can be seen in FIG. 12A, shielding 508 covers portions of the anode 504 and cathode 506 so the anode and cathode are present on only a portion of the radial surface of the electrode assembly 502. FIG. 12B illustrates anodes 504 and a cathode 506 in the form of small plates or tabs 512 located on the radial surface 510 of the percutaneous electrode assembly 502. While FIG. 12A illustrates an exemplary percutaneous electrode in multipolar configuration, the electrode may have a bipolar or monopolar configuration.

Next, FIG. 13 illustrates a side cross-sectional view of an exemplary percutaneous electrode assembly 502 including a lumen or passageway 512 for delivering fluid therethrough. The percutaneous electrode 502 may define a lumen or passageway 512 through the electrode to channel a fluid through the electrode and may further define openings 514 in communication with the lumen or passageway 512 to deliver fluid out through the electrode 502. Desirably, the electrode assembly defines openings 514 adjacent the anode 504 and cathode 506. However, these openings 514 may be at other locations. The lumen or pathway 512 may be integrated with or connected to a tube to deliver fluid to the lumen. The delivery tube can have a standard Luer connection or similar connection.

As can be seen in this illustration, the anodes 504 are paired or joined by a lead 520 and the cathode 506 is connected to a different lead 522. The electrode assembly may be connected to a fluid flow path in communication with a fluid pump; the fluid flow path may be configured to deliver a fluid to be dispensed to a patient through the electrode assembly. Alternatively and/or additionally, the electrode assembly may be connected to a bolus reservoir in communication with a bolus flow path. The bolus reservoir may be configured to selectively permit fluid to be dispensed to a patient through the electrode assembly. The arrangement may include a patient operable actuator configured to dispense fluid from the bolus reservoir. In such configuration, the percutaneous electrode can be used to deliver medicinal fluid such as liquid anesthetic in addition to the electrical stimulation. The medicinal liquid may be a bolus of anesthetic or it may be an antibiotic material, antimicrobial material or an electrolytic solution to enhance delivery of the electrical signal. Exemplary fluid pumps, fluid flow paths and bolus delivery configurations or systems are described in U.S. Pat. No. 6,981,967 issued Jan. 3, 2006 to Massengale et al., for "Large Volume Bolus Device and Method", incorporated herein by reference.

The aforementioned electrodes 20, 28 or electrode assembly 502 can be used to deliver percutaneous electrical stimulation to the target nerve tissue at a current ranging from about 0.1 milliamps to about 60 milliamps, such as from about 0.5 milliamps to about 30 milliamps, such as from about 1 milliamp to about 15 milliamps, such as from about 1.5 milliamps to about 10 milliamps. Alternatively, the electrical stimulation can be applied at a voltage ranging from about 0.1 volts to about 200 volts, such as from about 1 volt to about 150 volts, such as from about 5 volts to about 125 volts, such as from about 10 volts to about 100 volts.

Moreover, each electrical stimulation pulse can have a pulse width ranging from about 0.1 milliseconds to about 250 milliseconds, such as from about 0.5 milliseconds to about 150 milliseconds, such as from about 1 millisecond to about 75 milliseconds, such as from about 2.5 milliseconds to about 25 milliseconds.

Further, regardless of the particular type of article (e.g., external, implantable, etc.) and electrodes used (e.g., transcutaneous, percutaneous, etc.), the electrical stimulation can be applied over a course of treatment sessions that can occur on a daily, weekly, or monthly basis or as otherwise needed to relieve pain and restore sensation around the target nerve tissue being treated. Each treatment session can each last from about 5 minutes to about 12 hours, such as from about 15 minutes to about 10 hours, such as from about 30 minutes to about 8 hours, or for as short or long of a duration as tolerated by the patient and/or to provide relief to the patient. In some embodiments, twelve one-hour treatment sessions can be administered over a twelve-week period. In still other embodiments, the treatment can be administered multiple times per day, week, month, or year. For instance, in one particular embodiment, the treatment can be administered more than one time per day, such as up to about 3 times per day. In any event, the electrical field stimulation discussed above can, over time, be customized to treat an individual patient's peripheral neuropathy.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

What is claimed is:

1. An article for transcutaneously applying electrical stimulation to target nerve tissue to treat a patient having peripheral neuropathy, the article comprising:
    a support on which at least one electrode pair is positioned;
    a pulse generator attached to the at least one electrode pair via one or more leads; and
    a power supply connected to the pulse generator, wherein the article is configured to deliver electrical stimulation to the target nerve tissue via the at least one electrode pair at a level sufficient to initiate vasodilation of vasculature within or adjacent the target nerve tissue, wherein the vasculature is responsible for perfusing the target nerve tissue, wherein the electrical stimulation is delivered with a carrier frequency in the range of 25 kHz to 500 kHz.

2. The article of claim 1, wherein the power supply is connected to the support.

3. The article of claim 1, wherein the support is a wrap, a sock, a glove, or a finger cot.

4. The article of claim 3, wherein the wrap, the sock, the glove, or the finger cot is constructed from a molded material or from a nonwoven material.

5. The article of claim 1, wherein the peripheral neuropathy is diabetic peripheral neuropathy.

6. The article of claim 1, wherein the target nerve tissue is located within or adjacent a peripheral nerve.

7. The article of claim 1, wherein the target nerve tissue is located within a foot, a hand, a distal phalanx of a toe, a distal phalanx of a finger, or a combination thereof.

8. The article of claim 1, wherein the article is configured to initiate vasodilation of resistance-sized blood vessels having a lumen diameter of less than 400 micrometers.

9. The article of claim 1, wherein the article relieves pain caused by the peripheral neuropathy or facilitates recovery of a loss of sensation resulting from the peripheral neuropathy.

10. The article of claim 1, wherein the article is configured to deliver the electrical stimulation at a frequency ranging from about 0.1 Hertz to about 200 Hertz.

11. The article of claim 1, wherein the article is configured to deliver the electrical stimulation at a current ranging from about 0.1 milliamps to about 60 milliamps or at a voltage ranging from 0.1 volts to about 200 volts.

12. The article of claim 1, wherein the article is configured to deliver the electrical stimulation as a series of pulses each having a pulse width ranging from about 0.1 milliseconds to about 250 milliseconds.

13. The article of claim 1, wherein each electrode of the at least one electrode pair is formed by at least one of sputtering, reactive sputtering, physical vapor deposition, plasma deposition, chemical vapor deposition (CVD), printing, or spraying.

14. The article of claim 1, wherein each electrode of the at least one electrode pair is woven into a material of the support or is formed by screen printing.

15. The article of claim 1, wherein the one or more leads are between 0.25 and 100 microns thick.

16. The article of claim 15, wherein the one or more leads are woven into a material of the support.

17. A method for transcutaneously applying electrical stimulation to target nerve tissue to treat a patient having peripheral neuropathy, the method comprising:
    positioning at least one electrode pair adjacent an area of skin overlying the target nerve tissue; and
    delivering electrical stimulation to the target nerve tissue via the at least one electrode pair, wherein:
        the electrical stimulation is delivered at a level sufficient to initiate vasodilation of vasculature within or adjacent the target nerve tissue,
        the vasculature is responsible for perfusing the target nerve tissue, and the electrical stimulation is delivered with a carrier frequency in the range of 25 kHz to 500 kHz.

18. The method of claim 17, wherein the at least one electrode pair is positioned on a support.

19. The method of claim 18, wherein the support is a wrap, a sock, a glove, or a finger cot.

20. The method of claim 19, wherein the wrap, the sock, the glove, or the finger cot is constructed from a molded material or from a nonwoven material.

21. The method of claim 17, wherein the peripheral neuropathy is diabetic peripheral neuropathy.

22. The method of claim 17, wherein the target nerve tissue is located within or adjacent a peripheral nerve.

23. The method of claim 17, wherein the target nerve tissue is located within a foot, a hand, a distal phalanx of a toe, a distal phalanx of a finger, or a combination thereof.

24. The method of claim 17, wherein the electrical stimulation is delivered at a level sufficient to initiate vasodilation of resistance-sized blood vessels having a lumen diameter of less than 400 micrometers.

25. The method of claim 17, wherein the method relieves pain caused by the peripheral neuropathy or facilitates recovery of a loss of sensation resulting from the peripheral neuropathy.

26. The method of claim 17, wherein the electrical stimulation is delivered at a frequency ranging from about 0.1 Hertz to about 200 Hertz.

27. The method of claim 17, wherein the electrical stimulation is delivered at a current ranging from about 0.1 milliamps to about 60 milliamps or at a voltage ranging from about 0.1 volts to about 200 volts.

28. The method of claim 17, wherein the electrical stimulation is delivered as a series of pulses each having a pulse width ranging from about 0.1 milliseconds to about 250 milliseconds.

* * * * *